US012648951B2

(12) United States Patent
Szmulewitz et al.

(10) Patent No.: US 12,648,951 B2
(45) **Date of Patent: *Jun. 9, 2026**

(54) METHODS OF TREATING CASTRATION-RESISTANT PROSTATE CANCER WITH GLUCOCORTICOID RECEPTOR ANTAGONISTS, ANDROGEN DEPRIVATION THERAPY AND ANTI-ANDROGEN RECEPTOR THERAPY

(71) Applicant: University of Chicago, Chicago, IL (US)

(72) Inventors: Russell Z. Szmulewitz, Chicago, IL (US); Suzanne D. Conzen, Park Ridge, IL (US)

(73) Assignee: University of Chicago, Chicago, IL (US)

( * ) Notice: Subject to any disclaimer, the term of this patent is extended or adjusted under 35 U.S.C. 154(b) by 623 days.

This patent is subject to a terminal disclaimer.

(21) Appl. No.: 18/088,400

(22) Filed: Dec. 23, 2022

(65) Prior Publication Data

US 2023/0218634 A1     Jul. 13, 2023

Related U.S. Application Data

(63) Continuation of application No. 16/913,916, filed on Jun. 26, 2020, now Pat. No. 11,564,932, which is a continuation of application No. 16/374,157, filed on Apr. 3, 2019, now Pat. No. 10,729,699, which is a continuation of application No. 15/704,726, filed on Sep. 14, 2017, now Pat. No. 10,300,076, which is a continuation of application No. 15/013,660, filed on Feb. 2, 2016, now Pat. No. 9,801,893, which is a continuation of application No. 14/380,606, filed as application No. PCT/US2013/027150 on Feb. 21, 2013, now Pat. No. 9,289,436.

(60) Provisional application No. 61/603,137, filed on Feb. 24, 2012.

(51) Int. Cl.

| | |
|---|---|
| *A61K 31/567* | (2006.01) |
| *A61K 31/4166* | (2006.01) |
| *A61K 31/437* | (2006.01) |
| *A61K 31/569* | (2006.01) |
| *A61K 31/573* | (2006.01) |
| *A61K 45/06* | (2006.01) |
| *A61N 5/10* | (2006.01) |

(52) U.S. Cl.
CPC ........ *A61K 31/567* (2013.01); *A61K 31/4166* (2013.01); *A61K 31/437* (2013.01); *A61K 31/569* (2013.01); *A61K 31/573* (2013.01); *A61K 45/06* (2013.01); *A61N 5/10* (2013.01)

(58) Field of Classification Search
CPC .............. A61K 31/567; A61K 2300/00; A61K 31/573; A61P 35/00; A61P 35/04
See application file for complete search history.

(56) References Cited

U.S. PATENT DOCUMENTS

| | | | |
|---|---|---|---|
| 8,658,128 | B2 | 2/2014 | Altschul et al. |
| 9,114,147 | B2 | 8/2015 | Altschul et al. |
| 9,289,436 | B2 | 3/2016 | Szmulewitz et al. |
| 9,314,473 | B2 | 4/2016 | Altschul et al. |
| 9,801,893 | B2 | 10/2017 | Szmulewitz et al. |
| 10,300,076 | B2 | 5/2019 | Szmulewitz et al. |
| 10,729,699 | B2 | 8/2020 | Szmulewitz et al. |
| 11,564,932 | B2 | 1/2023 | Szmulewitz et al. |
| 2007/0128627 | A1 | 6/2007 | Simons, Jr. et al. |
| 2009/0156672 | A1 | 6/2009 | Budunova et al. |
| 2011/0269728 | A1 | 11/2011 | Pan et al. |
| 2012/0022121 | A1 | 1/2012 | Dalton et al. |
| 2015/0010503 | A1 | 1/2015 | Szmulewitz et al. |
| 2016/0151388 | A1 | 6/2016 | Szmulewitz et al. |
| 2018/0036318 | A1 | 2/2018 | Szmulewitz et al. |

FOREIGN PATENT DOCUMENTS

WO          2023088358 A1      5/2023

OTHER PUBLICATIONS

European Patent Application No. 21183080.7 , "Office Action", Jun. 29, 2023, 8 pages.
Antonarakis et al., "Emerging Therapeutic Approaches in the Management of Metastatic Castration Resistant Prostate Cancer", Prostate Cancer and Prostatic Diseases, vol. 14, Sep. 2011, pp. 206-218.
Arora et al., "Glucocorticoid Receptor Confers Resistance to Antiandrogens by Bypassing Androgen Receptor Blockade", Cell, vol. 155, No. 6, Dec. 5, 2013, pp. 1309-1322.
Attard et al., "Translating Scientific Advancement into Clinical Benefit for Castration-Resistant Prostate Cancer Patients", Clinical Cancer Research, vol. 1, No. 12, Jun. 15, 2011, pp. 3867-3875.
Belova et al., "Glucocorticoid Receptor Expression in Breast Cancer Associates with Older Patient Age", Breast Cancer Research and Treatment, vol. 116, No. 3, Aug. 2009, pp. 441-447.
Bolton et al., "Cell- and Gene-Specific Regulation of Primary Target Genes by the Androgen Receptor", Genes Development, vol. 21, No. 16, Aug. 15, 2007, pp. 2005-2017.
Chan et al., "Prognostic Significance of Gleason Score 3+4 versus Gleason Score 4+3 Tumor at Radical Prostatectomy", Adult Urology, vol. 56, No. 5, Nov. 2000, pp. 823-827.
Chen et al., "Androgen and Glucocorticoid Receptor Heterodimer Formation: A Possible Mechanism for Mutual Inhibition of Transcriptional Activity", Journal of Biological Chemistry, vol. 272, No. 22, May 30, 1997, pp. 14087-14092.
Chi et al., "Castration-Resistant Prostate Cancer: From New Pathophysiology to New Treatment Targets", European Urology, vol. 56, No. 4, Oct. 2009, pp. 594-605.
Clark et al., "1H-Pyrazolo[3,4-g]Hexahydro-Isoquinolines as Selective Glucocorticoid Receptor Antagonists with High Functional Activity", Bioorganic & Medicinal Chemistry Letters, vol. 18, No. 4, Feb. 15, 2008, pp. 1312-1317.

(Continued)

*Primary Examiner* — Elly-Gerald Stoica

(74) *Attorney, Agent, or Firm* — James Fox; Kilpatrick Townsend & Stockton LLP

(57) ABSTRACT

Embodiments of the invention are directed to the treatment of subjects with prostate cancer, in particular those with castration resistant prostate cancer, with glucocorticoid receptor antagonists. The prostate cancer may be one that has become resistant to androgen deprivation therapy, for example, by increase in glucocorticoid receptor expression and/or activity.

13 Claims, 3 Drawing Sheets

(56)                    References Cited

OTHER PUBLICATIONS

Cleutjens et al., "Both Androgen Receptor and Glucocorticoid Receptor Are Able to Induce Prostate-Specific Antigen Expression, but Differ in Their Growth-Stimulating Properties of LNCaP Cells", Endocrinology, vol. 138, No. 12, Dec. 1, 1997, pp. 5293-5300.

Davies et al., "Association of Glucocorticoid Receptors with Prostate Nuclear Sites for Androgen Receptors and with Androgen Response Elements", Journal of Molecular Endocrinology, vol. 5, No. 2, Oct. 1990, pp. 117-127.

Dayyani et al., "Novel Therapy For Metastatic Castrate-resistant Prostate Cancer", J. Natl. Cancer Inst. 103, 2011, pp. 1665-1675.

De Bono et al., "Abiraterone and Increased Survival in Metastatic Prostate Cancer", New England Journal of Medicine, vol. 364, No. 21, May 26, 2011, 19 pages.

Di Lorenzo et al., "Castration-Resistant Prostate Cancer", Drugs, vol. 70, No. 8, May 2010, pp. 983-1000.

Donovan et al., "Androgen Receptor Expression is Associated with Prostate Cancer-Specific Survival in Castrate Patients with Metastatic Disease", Bob Jones University International, vol. 105, No. 4, Feb. 2010, pp. 462-467.

Efstathiou et al., "Molecular Characterization of Enzalutamide-treated Bone Metastatic Castration-resistant Prostate Cancer", European Urology, vol. 67, No. 1, Jan. 2015, pp. 53-60.

European Application No. 13751132.5 , Extended European Search Report, Mailed On Mar. 21, 2016, 14 pages.

European Application No. 13751132.5 , "Partial Supplementary European Search Report", Sep. 7, 2015, 6 pages.

European Application No. 16183642.4 , Extended European Search Report, Mailed On Dec. 1, 2016, 12 pages.

Euroepan Application No. 21183080.7 , Extended European Search Report, Mailed On Oct. 21, 2021, 12 pages.

Fakih et al., "Glucocorticoids and Treatment of Prostate Cancer: A Preclinical and Clinical Review", Urology, vol. 60, No. 4, Oct. 2002, pp. 553-561.

Fiorentino et al., "Blood and Tissue Biomarkers in Prostate Cancer: State of the Art", Urologic Clinics of North America, vol. 37, No. 1, Feb. 2010, pp. 1-14.

Fradet , "PSA and Beyond: Biomarkers in Prostate Cancer Diagnosis and Prognosis", Current Opinion in Urology, vol. 19, No. 3, May 2009, pp. 243-246.

Guo et al., "A Novel Androgen Receptor Splice Variant Is Up-Regulated During Prostate Cancer Progression and Promotes Androgen Depletion-Resistant Growth", Cancer Research, vol. 69, No. 6, Mar. 15, 2009, pp. 2305-2313.

Han et al., "Biochemical (Prostate Specific Antigen) Recurrence Probability Following Radical Prostatectomy for Clinically Localized Prostate Cancer", The Journal of Urology, vol. 169, No. 2, Feb. 2003, pp. 517-523.

Hinrichs et al., "Glucocorticoids Do Not Inhibit Antitumor Activity of Activated CD8+ T Cells", Journal of Immunotherapy, Voliume 28, No. 6, 2005, 17 pages.

Ho et al., "A Complex Response Element in Intron 1 of the Androgen-Regulated 20-kDa Protein Gene Displays Cell Type-Dependent Androgen Receptor Specificity", Journal of Biological Chemistry, vol. 268, No. 36, Dec. 25, 1993, pp. 27226-27235.

Isikbay et al., "Glucocorticoid Receptor Activity Contributes to Resistance to Androgen-Targeted Therapy in Prostate Cancer", Hormones and Cancer, vol. 5, No. 2, Apr. 2014, pp. 72-89.

Jemal et al., "Cancer Statistics", CA: A Cancer Journal for Clinicians, vol. 60, No. 5, Sep.-Oct. 2010, pp. 277-300.

Kach et al., "Selective Glucocorticoid Receptor Modulators (SGRMs) Delay Castrate- Resistant Prostate Cancer Growth", Molecular Cancer Therapeutics, vol. 16, No. 8, Aug. 2017, pp. 1680-1692.

Karantanos et al., "Understanding the Mechanisms of Androgen Deprivation Resistance in Prostate Cancer at the Molecular Level", European Urology, vol. 67, No. 1, 2015, pp. 470-479.

Kim et al., "Current Treatment Strategies for Castration-Resistant Prostate Cancer", Korean Journal of Urology, vol. 52, No. 3, Mar. 2011, pp. 157-165.

Klein et al., "Analyzing Survival Curves at a Fixed Point in Time", Statistics in Medicine, vol. 26, No. 24, Oct. 30, 2007, pp. 4505-4519.

Koochenkpour , "Androgen Receptor Signaling and Mutations in Prostate Cancer", Asian Journal of Andrology, vol. 12, No. 5, Sep. 2010, pp. 639-657.

Li et al., "High Level of Androgen Receptor is Associated with Aggressive Clinicopathologic Features and Decreased Biochemical Recurrence-Free Survival in Prostate: Cancer Patients Treated with Radical Prostatectomy", The American Journal of Surgical Pathology, vol. 28, No. 7, Jul. 2004, pp. 928-934.

Lotan et al., "Up-Regulation of MKK4, MKK6 and MKK7 During Prostate Cancer Progression: An Important Role for SAPK Signalling in Prostatic Neoplasia", The Journal of Pathology, vol. 212, No. 4, Aug. 2007, pp. 386-394.

Makarov et al., "Updated Nomogram to Predict Pathologic Stage of Prostate Cancer Given Prostate-Specific Antigen Level, Clinical Stage, and Biopsy Gleason Score (Partin Tables) Based on Cases from 2000 to 2005", Urology, vol. 69, No. 6, Jun. 2007, pp. 1095-1101.

Mikosz et al., "Glucocorticoid Receptor-Mediated Protection from Apoptosis is Associated with Induction of the Serine/Threonine Survival Kinase Gene, sgk-1", The Journal of Biological Chemistry, vol. 276, No. 20, May 18, 2001, pp. 16649-16654.

Mohler et al., "Androgen and Glucocorticoid Receptors in the Stroma and Epithelium of Prostatic Hyperplasia and Carcinoma", Clinical Cancer Research, vol. 2, No. 5, May 1996, pp. 889-895.

Montgomery et al., "Impact of Baseline Corticosteroids on Survival and Steroid Androgens in Metastatic Castration-Resistant Prostate Cancer: Exploratory Analysis from COU-AA-301", Eur. Urology, vol. 67, No. 5, 2014, 8 pages.

Mottet et al., "EAU Guidelines on Prostate Cancer. Part II: Treatment of Advanced, Relapsing, and Castration-Resistant Prostate Cancer", European Urology, vol. 59, Jan. 2011, pp. 572-583.

Niemeier et al., "Androgen Receptor in Breast Cancer: Expression in Estrogen Receptor-Positive Tumors and in Estrogen Receptor-Negative Tumors with Apocrine Differentiation", Modern Pathology, vol. 23, No. 2, Feb. 2010, pp. 205-212.

Ohlmann et al., "Novel Options for the Treatment of Castration-Resistant Prostate Cancer", World Journal of Urology, vol. 30, No. 4, Aug. 2012, pp. 495-503.

International Patent Application No. PCT/US2013/027150 , International Preliminary Report on Patentability, Mailed On Sep. 4, 2014, 7 pages.

International Patent Application No. PCT/US2013/027150 , International Search Report and Written Opinion, Mailed On Apr. 29, 2013, 9 pages.

Petrylak et al., "Evaluation of Prostate-Specific Antigen Declines for Surrogacy in Patients Treated on SWOG 99-16", Journal of the National Cancer Institute, vol. 98, No. 8, Apr. 19, 2006, pp. 516-521.

Pound et al., "Natural History of Progression after PSA Elevation Following Radical Prostatectomy", JAMA, vol. 281, No. 17, May 5, 1999, pp. 1591-1597.

Rauhala et al., "Dual-Specificity Phosphatase 1 and Serum/Glucocorticoid-Regulated Kinase are Downregulated in Prostate Cancer", International Journal of Cancer, vol. 117, No. 5, Dec. 10, 2005, pp. 738-745.

Rosner et al., "Higher Tumor to Benign Ratio of the Androgen Receptor mRNA Expression Associates with Prostate Cancer Progression after Radical Prostatectomy", Urology, vol. 70, No. 6, Dec. 2007, pp. 1225-1229.

Sahoo et al., "Coordinate Expression of the PI3-Kinase Downstream Effectors Serum and Glucocorticoid-Induced Kinase (SGK-1) and Akt-1 in Human Breast Cancer", European Journal of Cancer, vol. 41, No. 17, Nov. 2005, pp. 2754-2759.

Sahu et al., "FoxA1 Specifies Unique Androgen and Glucocorticoid Receptor Binding Events in Prostate Cancer Cells", Cancer Research, vol. 73, No. 5, Mar. 2013, pp. 1570-1580.

(56)                    References Cited

OTHER PUBLICATIONS

Scher et al., "Antitumour Activity of MDV3100 in Castration-Resistant Prostate Cancer: A Phase 1-2 Study", Lancet, vol. 375, No. 9724, Apr. 24, 2010, pp. 1437-1446.

Scher et al., "Biology of Progressive, Castration-Resistant Prostate Cancer: Directed Therapies Targeting the Androgen-Receptor Signaling Axis", Journal of Clinical Oncology, vol. 23, No. 32, Nov. 10, 2005, pp. 8253-8261.

Scher et al., "End Points and Outcomes in Castration-Resistant Prostate Cancer: From Clinical Trials to Clinical Practice", Journal of Clinical Oncology, vol. 29, No. 27, Sep. 20, 2011, pp. 3695-3704.

Seruga et al., "Drug Resistance in Metastatic Castration-Resistant Prostate Cancer", Nature Reviews Clinical Oncology, vol. 8, No. 1, Jan. 2011, pp. 12-23.

Shanmugam et al., "Serum/Glucocorticoid-Induced Protein Kinase-1 Facilitates Androgen Receptor-Dependent Cell Survival", Cell Death Differ, vol. 14, No. 12, Oct. 12, 2007, pp. 2085-2094.

Sherk et al., "Development of a Small Molecule Serum and Glucocorticoid-Regulated Kinase 1 Antagonist and its Evaluation as a Prostate Cancer Therapeutic", Cancer Research, vol. 68, No. 18, Sep. 15, 2008, pp. 7475-7483.

Song et al., "Dihydrotestosterone Enhances Castration-Resistant Prostate Cancer Cell Proliferation through STAT5 Activation via Glucocorticoid Receptor Pathway", The Prostate, vol. 74, No. 12, Sep. 2014, pp. 1240-1248.

Srinivas et al., "Phase II Study Evaluating Oral Triamcinolone in Patients with Androgen-Independent Prostate Cancer", Adult Urology, vol. 67, No. 5, May 1, 2006, pp. 1001-1006.

Stephenson et al., "Preoperative Nomogram Predicting the 10-Year Probability of Prostate Cancer Recurrence After Radical Prostatectomy", Journal of the National Cancer Institute, vol. 98, No. 10, May 17, 2006, pp. 715-717.

Sterbis et al., "Higher Expression of the Androgen-Regulated Gene PSA/HK3 mRNA in Prostate Cancer Tissues Predicts Biochemical Recurrence-Free Survival", Clinical Cancer Research, vol. 14, No. 3, Feb. 2008, pp. 758-763.

Sun et al., "Castration Resistance in Human Prostate Cancer is Conferred by a Frequently Occurring Androgen Receptor Splice Variant", Journal of Clinical Investigation, vol. 120, No. 8, Aug. 2, 2010, pp. 2715-2730.

Szmulewitz et al., "Serum/Glucocorticoid-Regulated Kinase 1 Expression in Primary Human Prostate Cancers", Prostate, vol. 72, No. 2, Feb. 1, 2012, pp. 157-164.

Tannock et al., "Docetaxel Plus Prednisone or Mitoxantrone Plus Prednisone for Advanced Prostate Cancer", The New England Journal of Medicine, vol. 351, No. 15, Oct. 7, 2004, pp. 1502-1512.

Taplin et al., "A Phase II Study of Mifepristone (RU-486) in Castration-Resistant Prostate Cancer, with a Correlative Assessment of Androgen-Related Hormones", BJU International, vol. 101, No. 9, May 1, 2008, pp. 1084-1089.

Tessier et al., "Serum and Glucocorticoid-Regulated Protein Kinases: Variations on a Theme", Journal of Cellular Biochemistry, vol. 98, No. 6, Aug. 15, 2006, pp. 1391-1407.

Twiddy et al., "Cholesterol as a Potential Target for Castration-Resistant Prostate Cancer", Pharmaceutical Research, vol. 28, No. 3, Mar. 2011, pp. 423-437.

Ward et al., "Rising Prostate-Specific Antigen after Primary Prostate Cancer Therapy", Nature Clinical Practice Urology, vol. 2, No. 4, Apr. 1, 2005, pp. 174-182.

Wright et al., "Differences in Prostate Cancer Outcomes Between Cases With Gleason 4+3 and Gleason 3+4 Tumors in a Population-Based Cohort", The Journal of Urology, vol. 182, No. 6, Dec. 2009, pp. 2702-2707.

Wu et al., "Microarray Analysis Reveals Glucocorticoid-Regulated Survival Genes that are Associated with Inhibition of Apoptosis in Breast Epithelial Cells", Cancer Research, vol. 64, No. 5, Mar. 1, 2004, pp. 1757-1764.

Xie et al., "The Expression of Glucocorticoid Receptor is Negatively Regulated by Active Androgen Receptor Signaling in Prostate Tumors", Int. J. Cancer, vol. 136, 2015, pp. E27-E38.

Yan et al., "Relationship between Glucocorticoid Receptor Signal Pathway and Androgen-Independent Prostate Cancer", Urologia Internationalis, vol. 81, Issue 2, 2008, pp. 228-233.

Yemelyanov et al., "Differential Targeting of Androgen and Glucocorticoid Receptors Induces ER Stress and Apoptosis in Prostate Cancer Cells", Cell Cycle, vol. 11, No. 2, Jan. 15, 2012, pp. 395-406.

Yemelyanov et al., "Tumor Suppressor Activity of Glucocorticoid Receptor in the Prostate", Oncogene, vol. 26, No. 13, Mar. 22, 2007, pp. 1885-1896.

Zegarra-Moro et al., "Disruption of Androgen Receptor Function Inhibits Proliferation of Androgen-Refractory Prostate Cancer Cells", Cancer Research, vol. 62, No. 4, Feb. 15, 2002, pp. 1008-1013.

Zhao et al., "Glucocorticoid Receptor in Prostate Epithelia is not required for Corticosteroid-Induced Epithelial Hyperproliferation in the Mouse Prostate", The Prostate, vol. 74, 2014, pp. 1068-1078.

Zou et al., "Androgen-Induced Coactivator ANCCA Mediates Specific Androgen Receptor Signaling in Prostate Cancer", Cancer Research, vol. 69, No. 8, Apr. 2009, pp. 3339-3346.

Entire Population

Gleason Grade Subgroups

METHODS OF TREATING CASTRATION-RESISTANT PROSTATE CANCER WITH GLUCOCORTICOID RECEPTOR ANTAGONISTS, ANDROGEN DEPRIVATION THERAPY AND ANTI-ANDROGEN RECEPTOR THERAPY

The present application is a Continuation of U.S. application Ser. No. 16/913,916, filed Jun. 26, 2020, which is a Continuation of U.S. application Ser. No. 16/374,157, filed Apr. 3, 2019 (now U.S. Pat. No. 10,729,699, issued Aug. 4, 2020), which is a Continuation of U.S. application Ser. No. 15/704,726, filed Sep. 14, 2017 (now U.S. Pat. No. 10,300, 076, issued May 28, 2019), which is a Continuation of U.S. application Ser. No. 15/013,660, filed Feb. 2, 2016 (now U.S. Pat. No. 9,801,893, issued Oct. 31, 2017), which is a Continuation of U.S. application Ser. No. 14/380,606, filed Aug. 22, 2014 (now U.S. Pat. No. 9,289,436, issued Mar. 22, 2016), which is a U.S. national stage application under 35 U.S.C. § 371 of International Application No. PCT/ US2013/027150, filed Feb. 21, 2013, which claims the benefit of, and priority to, U.S. Provisional Patent Application Ser. No. 61/603,137, filed Feb. 24, 2012, the disclosures of which are hereby incorporated by reference in their entireties.

This invention was made with government support awarded by the Department of Defense and the National Institutes of Health. The government has certain rights in the invention.

BACKGROUND OF THE INVENTION

I. Field of the Invention

Embodiments of this invention are directed generally to biology and medicine. In certain aspects, methods and compositions for treating a prostate cancer patient with a glucocorticoid receptor (GR) antagonist are provided. More specifically, the methods comprise treating a subject with castration-resistant prostate cancer with a GR antagonist, in particular in a subject that has previously received and demonstrated prostate cancer progression despite androgen-deprivation therapy.

II. Background

Localized prostate cancers are treated with curative intent by surgery or radiation, however, as many as 40% of patients will develop recurrent disease over time, and it remains the second leading cause of cancer related death in men (Jemal et al., 2010; Ward and Moul, 2005). There are established predictors of prostate cancer recurrence or progression and widely used prognostic nomograms, which in large part utilize common pathologic criteria (Han et al., 2003; Pound et al., 1999; Makarov et al., 2007; Stephenson et al., 2006). Furthermore, there are multiple biomarkers in development to help further hone prostate cancer prognostication (Fradet, 2009; Fiorentino et al., 2010). Nonetheless, the biologic factors modulating prostate cancer biology and progression despite anti-androgen therapy remain an important area of research.

The majority of prostate cancers rely on the androgen receptor (AR) for cell survival and proliferation, and the pathway remains important in the progression of prostate cancer even in patients whose disease progresses despite androgen deprivation therapy (Zegarra-Moro et al., 2002; Scher and Sawyers, 2005). Recently, serum/glucocorticoid-regulated kinase 1 (SGK1) was found to be upregulated by AR activation in prostate cancer cell lines resulting in enhanced prostate cancer cell survival in vitro (Shanmugam et al., 2007; Zou et al., 2009; Bolton et al., 2007). SGK1 is a serine/threonine protein kinase with 54% homology in its catalytic domain to Akt and is involved in a multitude of metabolic and cell survival functions (Tessier and Woodgett, Jr., 2006). SGK1 is transcriptionally induced and its protein product plays an important role in cellular responses to stressors such as oxidation, heat, and ultraviolet radiation (Tessier and Woodgett, 2006). SGK1 has been shown to be overexpressed in a proportion of human breast cancers (Sahoo et al., 2005) and to be important in protection from stress-induced apoptosis in breast cancer cell lines (Mikosz et al., 2001; Wu et al., 2004). Similarly, androgen-sensitive prostate cancer cell lines that ectopically express SGK1 demonstrate increased survival following androgen-deprivation compared to those that do not overexpress the SGK1 (Shanmugam et al., 2007). In addition, in vitro studies using small interfering RNAs targeting SGK1 or small molecule pharmacologic inhibitors of SGK1 demonstrate that inhibition of SGK1 activity leads to decreased androgen-mediated prostate cancer cell growth (Shanmugam et al., 2007; Sherk et al., 2008). The inventors showed SGK1 expression is high in primary prostate cancers and reduced following anti-androgen therapy (Szmulewitz et al., 2010) To the inventors' knowledge, there has been only one other study examining SGK1 expression in primary human prostate tumors; somewhat surprisingly, SGK1 expression was significantly decreased in prostate cancers as compared to prostatic hypertrophy (Rauhala et al., 2005). In addition to the AR, SGK1 is also a direct target of glucocorticoid receptor (GR) activation in epithelial cells. Interestingly, standard chemotherapy regimens for castrate-resistant prostate cancer include glucocorticoids such as prednisone, a GR agonist (Tannock et al., 2004; Petrylak et al., 2006). Although a proportion of patients show responses by a reduction in the tumor marker PSA and obtain palliative benefits from glucocorticoid treatment, there are no phase III data demonstrating that glucocorticoids provide a survival benefit (Fakih et al., 2002). Therefore, it is unclear how glucocorticoids function in metastatic prostate cancer. To date, there are a few reports examining GR expression in human prostate cancer (Yemelyanov et al., 2007; Mohler et al., 1996) and no information on GR status in prostate cancer from androgen-deprived patients.

SUMMARY OF THE INVENTION

Embodiments concern methods, compositions, and apparati related to assessing, prognosing, and/or treating prostate cancer patients. In particular, it concerns using glucocorticoid receptor (GR) antagonists to treat patients with prostate cancer, in particular those with metastatic and castration resistant prostate cancer.

Some embodiments include generating an expression profile for glucocorticoid receptor (GR), which means obtaining the level of expression of AR or GR directly or indirectly by measuring or assaying activity or expression. Methods include directly measuring or assaying the level of expression or activity which refers to measuring or assaying a sample to determine the level of AR or GR expression (protein or transcript) in the cell. Indirectly obtaining the level of expression includes measuring or assaying expression or activity of a gene or protein that correlates with AR or GR expression or activity. In some embodiments, the level of AR or GR expression can be indirectly obtained by measuring or assaying expression of a AR- or GR-responsive gene, which refers to a gene whose expression is affected in a dose-dependent manner by AR or GR expression or activity. Expression refers to either protein expression or RNA (transcript) expression. Methods may involve either type of expression and a variety of assays are well known to those of skill in the art. For example, quantitative PCR may be performed to obtain RNA expression levels. The Affymetrix chip used in the Examples also provides information regarding RNA expression levels. Alternatively, reagents to detect protein expression levels may be employed in embodiments. Methods may involve probes, primers, and/or antibodies that are specific to GR or AR in order to assess expression levels.

In some embodiments, the activity level of GR is measured by assaying the level of GR expression. In additional embodiments, GR expression is GR transcript expression. In other embodiments, GR expression is GR protein expression. As discussed above, in some embodiments, the activity level of GR is measured by assaying the expression level of one or more GR-responsive genes. A GR-responsive gene may be one or more of the following: MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, or MAOA.

In some embodiments, there is a step of assaying or measuring the activity level of glucocorticoid receptor (GR) in a biological sample from the patient containing prostate cancer cells. As discussed above, the activity level of GR can be obtained directly or indirectly. It is specifically contemplated that levels of glucocorticoid activity or expression refers to activity or expression of the genes or proteins GR$\alpha$, GR$\beta$, or both. Unless specifically stated otherwise, the terms "glucocorticoid receptor" or "GR" refer to both forms. Embodiments discussed with respect to glucocorticoid receptor or GR may also be implemented solely with GR$\alpha$ or solely with GR$\beta$.

Methods may also include obtaining a level of androgen receptor (AR) expression in prostate cancer cells from the patient. The level can be obtained by obtaining the results of an assay that measured the level of AR expression. In some embodiments, the level is obtained by measuring or assaying the level of AR expression.

In one aspect of the invention, there is provided a method of treating castration-resistant prostate cancer in a subject comprising administering to said subject a glucocorticoid receptor (GR) antagonist. The subject may exhibit androgen-deprived prostate cancer, and/or may previously have been or is currently being treated with androgen deprivation therapy, such as with leuprolide goserelin, triptorelin, histrelin, degerelix or surgical castration. The subject may previously have been or is currently being treated with an androgen receptor (AR) antagonist, such as MDV3100, ARN-509, flutamide, bicalutamide, nilutamide, or cyproterone acetate. The subject may exhibits prostate cancer with elevated GR expression. The GR antagonist may be beclometasone, betamethasone, budesonide, ciclesonide, flunisolide, fluticasone, GSK650394, mifepristone, mometasone, or triamcinoclone. In further embodiments it may be CORT 0113083 or CORT 00112716.

The subject may be treated with a second prostate cancer therapy, such as androgen deprivation therapy, including leuprolide goserelin, triptorelin, histrelin, or surgical castration. The second prostate cancer therapy may be an androgen synthesis inhibitor, such as ketococonazole, abiraterone, TAK-700 and TOK001. The second prostate cancer therapy may be conventional chemotherapy, radiotherapy, cryotherapy, immunotherapy or surgery. The second prostate cancer therapy may be given prior to said GR antagonist, after said GR antagonist, or at the same time as said GR antagonist. The GR antagonist may administered systemically, regionally or locally to a tumor site, or may be administered orally, intravenously, intraarterially, into tumor vasculature or intratumorally. The GR antagonist is administered more than once, such as 2, 3, 4, 5, 6, 7, 8, 9, 10, 11, 12, 13, 14, 15, 20, 25 or more times.

The method may further comprising assessing GR expression in a prostate cancer tissue of said subject. The method may further comprising assessing androgen receptor expression in a prostate cancer tissue of said subject. The prostate cancer may be metastatic or recurrent. The subject may have previously been treated with both androgen-deprivation therapy and an androgen receptor antagonist.

In another embodiment, there is provided a method of inhibiting the progression of castration resistant prostate cancer in a subject comprising administering to said subject with a glucocorticoid receptor (GR) antagonist. A further embodiment comprises a method of preventing development of castration resistant prostate cancer in a subject comprising administering to said subject with a glucocorticoid receptor (GR) antagonist. Yet another embodiment comprise s method of inhibiting glucocorticoid receptor activity in prostate cancer tissues in a subject comprising administering to said subject with a GR antagonist. An additional embodiment comprises a method of treating castration resistant prostate cancer in a subject comprising administering to said subject with a glucocorticoid receptor (GR) antagonist and a steroid.

Another embodiment comprises a method of treating prostate cancer in a subject comprising co-administering to said subject an androgen receptor (AR) antagonist and a glucocorticoid receptor (GR) antagonist. Further, an embodiment may comprise a method of treating prostate cancer in a subject whose tumor become resistant to anti-AR therapy comprising add a glucocorticoid receptor (GR) antagonist to their therapy. Still yet an additional embodiment comprises a method of treating prostate cancer in a subject whose tumor become resistant to anti-AR therapy comprising co-administering to said subject a glucocorticoid receptor (GR) antagonist and a cytotoxic chemotherapy. A further embodiment involves a method of treating prostate cancer in a subject comprising co-administering to said subject a glucocorticoid receptor (GR) antagonist and a drug that decreases circulating levels of testosterone. Another embodiment comprises a method of treating prostate cancer in a subject comprising alternating administrations to said subject of an androgen receptor (AR) antagonist and a glucocorticoid receptor (GR) antagonist.

Embodiments may also include where the patient is treated with more than one type of cancer therapy. This may be after the patient is determined to have a particular prognosis or after the status of the patient's GR and AR expression profile is known. In some embodiments, a patient is treated with at least two of the following: radiation, chemotherapy, or a biologic. In particular embodiments, the patient may be treated with an anti-androgen, kinase inhibitor and/or anti-angiogenic agent.

In another embodiment, the method may comprises alternating AR antagonism and GR antagonism. The methods may therefore address tumor shift back and forth between signaling mechanisms that overcome receptor blockade. For example, the methods may include AR antagonist therapy followed by GR antagonist therapy, following by AR antagonist therapy, followed by GR antagonist therapy, and so on.

Any method may also include treating the patient for prostate cancer, which may include directly administering or providing a cancer therapy. In some embodiments, a practitioner or doctor may prescribe a cancer therapy that the patient administers to herself.

To achieve these methods, a doctor, medical practitioner, or their staff may retrieve a biological sample from a patient for evaluation. The sample may be a biopsy, such as a prostate tissue or tumor biopsy. The sample may be analyzed by the practitioner or their staff, or it may be sent to an outside or independent laboratory. The medical practitioner may be cognizant of whether the test is providing information regarding the patient's level of GR and/or AR expression or activity, or the medical practitioner may be aware only that the test indicates directly or indirectly that the test reflects that the patient has a particular prognosis or can be given a particular prognosis score. Furthermore, the practitioner may know the patient's AR or GR status, such as AR+ or AR−, or GR+ or GR−. Alternatively, he or she may be aware only that the test or assay indicates the patient has a poor prognosis, or the worst prognosis.

Other embodiments include a computer readable medium having software modules for performing a method comprising the acts of: (a) comparing glucocorticoid receptor data obtained from a patient's prostate cancer sample with a reference; and (b) providing an assessment of glucocorticoid receptor status to a physician for use in determining an appropriate therapeutic regimen for a patient. In further embodiments, the computer readable medium further comprises a software module for assessing estrogen receptor status of the patient's prostate cancer sample.

Computer systems are also included. In some embodiments, they have a processor, memory, external data storage, input/output mechanisms, a display, for assessing glucocorticoid receptor activity, comprising: (a) a database; (b) logic mechanisms in the computer generating for the database a GR-responsive gene expression reference; and (c) a comparing mechanism in the computer for comparing the GR-responsive gene expression reference to expression data from a patient sample using a comparison model to determine a GR gene expression profile of the sample.

Other embodiments include an internet accessible portal for providing biological information constructed and arranged to execute a computer-implemented method for providing: (a) a comparison of gene expression data of one or more GR-responsive genes in a patient sample with a calculated reporter index; and (b) providing an assessment of GR activity or expression to a physician for use in determining an appropriate therapeutic regime for a patient.

In addition to compiling, collecting and or processing data related to GR status, methods, media and systems may also include the same embodiments with respect to data related to AR status. Such aspects may be instead of or in addition to the aspects related to GR status or data.

Embodiments also include methods of killing prostate cancer cells comprising administering to a prostate cancer patient an effective amount of a combination of anti-cancer compounds, wherein the anticancer compounds comprise a glucocorticoid receptor antagonist and a chemotherapeutic. In other embodiments, there are methods for treating prostate cancer in a patient comprising administering to the patient an effective amount of glucocorticoid receptor antagonist and a chemotherapeutic. In further embodiments, methods are provided for treating chemotherapy-insensitive prostate cancer cells comprising administering to a prostate cancer patient an effective amount of a glucocorticoid receptor antagonist followed by chemotherapy.

Other methods include methods for treating prostate cancer in a patient comprising: a) administering radiation or at least a first chemotherapeutic to the patient; b) subsequently administering an effective amount of a glucocorticoid receptor antagonist to the patient; and, c) administering radiation again or at least a second chemotherapeutic to the patient after the glucocorticoid receptor antagonist is administered to the patient.

In some embodiments, there are methods for treating prostate cancer in a patient comprising: a) administering an effective amount of a glucocorticoid receptor antagonist to the patient, wherein the patient expresses detectable levels of GR prior to administration of the GR antagonist; b) then administering an effective amount of radiation or at least one chemotherapeutic.

It is contemplated that in methods described herein, prostate cancer cells may undergo apoptosis following treatment set forth herein. Moreover, in some embodiments, the combination of a glucocorticoid receptor antagonist and an anticancer agent or compound induces more apoptosis than treatment with just the anticancer treatment alone.

Glucocorticoid receptor antagonists are known to those of skill in the art. It refers to a compound or substance that that does not provoke a biological response itself upon binding to the glucocorticoid receptor, but blocks or dampens agonist-mediated responses. Examples include, but are not limited to, beclometasone, betamethasone, budesonide, ciclesonide, flunisolide, fluticasone, mifepristone, mometasone, and triamcinolone. In further embodiments it may be CORT 0113083 or CORT 00112716. In additional embodiments, the glucocorticoid receptor antagonist has undetectable level or a lower level of activity as a progesterone receptor antagonist. In certain embodiments, the glucocorticoid receptor antagonist has greater than 10-fold, 50-fold, 100-fold, 200-fold, 300-fold, 400-fold, 500-fold, 1000-fold lower binding activity (or any range derivable therein) for another hormone receptor compared to its binding activity for glucocorticoid receptor. In specific embodiments the hormone receptor is estrogen receptor or progesterone receptor.

In some embodiments, a patient had been previously treated with an anti-cancer therapy, such as radiation, chemotherapy, or immunotherapy (or a combination or multiple therapies thereof). In certain embodiments, a first anticancer therapy prior to therapy with glucocorticoid receptor antagonist was last administered more than two weeks prior to the glucocorticoid receptor antagonist or its combination with a second anti-cancer therapy. In certain embodiments, this first anti-cancer therapy that does not include a glucocorticoid receptor antagonist was last administered to the prostate cancer patient at least 7, 8, 9, 10, 11, 12, 13, 14 days, and/or 1, 2, 3, 4, or 5 weeks, and/or 1, 2, 3, 4, 5, 6, 7, 8, 9, 10, 11, or 12 months prior to treatment with a glucocorticoid receptor antagonist. Treatment methods may be applied to prostate cancer or prostate cancer cells that are chemo-resistant or prostate cancer cells that are not chemo-sensitive. Moreover, treatment may be applied to prostate cancer or to prostate cancer cells that were previously administered a first apoptosis inducing agent, but were resistant to apoptosis.

Methods involve treating prostate cancer, particularly an AR antagonist-resistant prostate cancer, with a combination of therapies that includes a glucocorticoid receptor antagonist and an anticancer therapy that induces apoptosis (together they may be referred to as a combination of anticancer agents or compounds), such as a chemotherapeutic or an anti-androgen receptor (AR) antagonist such as MDV-3100. In some embodiments, the chemotherapeutic is capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, or vinorelbine, or a combination of these agents. In other embodiments, therapy with a glucocorticoid receptor antagonist is combined MDV-3100, abiraterone, radiation, chemotherapeutic(s) and radiation, a combination of chemotherapeutics, or a combination of one or more chemotherapeutic agents and an anti-androgen or anti-androgen receptor drug.

It is contemplated that in some embodiments of the combination therapy the glucocorticoid receptor antagonist is administered within 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof within administration of at least one or the combination of the anti-cancer agents or compounds. In specific embodiments, the glucocorticoid receptor antagonist is administered within 2 hours, 12 hours or 24 hours of administration of an anticancer agent or compound (or a combination of such agents or compounds).

In a further embodiment, the glucocorticoid receptor (GR) antagonists of the present invention can be combined with anti-kinases such as mammalian target of rapamycin (mTOR) inhibitors. Non-limiting examples of mTOR inhibitors include rapamycin, epigallocatechin gallate (EGCG), caffeine curcumin, resveratrol, temsirolimus, everolimus, and ridaforolimus, and derivatives and analogues thereof. This combination can be used in compositions and methods disclosed throughout the specification.

It is specifically contemplated that treatment may continue or be repeated. In some embodiments, once treated with the combination of a glucocorticoid receptor antagonist and at least one anticancer agent or compound, all or part of the treatment may be repeated alone or in combination with a different anticancer agent or compound.

In certain embodiments, the glucocorticoid receptor antagonist is administered prior to as the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof prior to administration of at least one or the combination of the anti-cancer agents or compounds. It is specifically contemplated that in some embodiments, the glucocorticoid receptor antagonist is given prior to administration of the anticancer agent or compound but that the glucocorticoid receptor antagonist is also given concurrently with or after administration of the initial or a subsequent dose of the anticancer agent or compound. As discussed throughout, the anticancer agent or compound may be in a combination of such agents or compounds. In certain embodiments, the glucocorticoid receptor antagonist is administered up to three days prior to administering the anticancer agent or compound.

Additionally or alternatively, the glucocorticoid receptor antagonist is administered after administration of the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof after administration of at least one or the combination of the anti-cancer agents or compounds. It is specifically contemplated that in some embodiments, the glucocorticoid receptor antagonist is given after to administration of the anticancer agent or compound; such administration may be repeated. As discussed throughout, the anticancer agent or compound may be in a combination of such agents or compounds. In certain embodiments, the glucocorticoid receptor antagonist is administered up to three days after administering the anticancer agent or compound.

Compositions are contemplated to include a glucocorticoid receptor antagonist and any other anticancer compound discussed herein. In some embodiments, the composition is in a pharmaceutically acceptable formulation.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments that are applicable to all aspects of the technology described herein.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

In certain aspects, prognosis is an estimation of the likelihood of metastasis free survival of said patient over a predetermined period of time, e.g., over a period of 5 years.

In further aspects, prognosis is an estimation of the likelihood of death of disease of said patient over a predetermined period of time, e.g., over a period of 5 years.

The term "recurrence" refers to the detection of prostate cancer in form of metastatic spread of tumor cells, local recurrence, contralateral recurrence or recurrence of prostate cancer at any site of the body of the patient after prostate cancer had been substantially undetectable or responsive to treatments.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress," "overexpression," "overexpressed," "up-regulate," or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels of transcription or translation in comparison to a non-cancer cell or cancer cell that is not associated with the worst or poorest prognosis.

"Biological sample" includes sections of tissues such as biopsy and autopsy samples, and frozen sections taken for histologic purposes. Such samples include prostate cancer tissues, cultured cells, e.g., primary cultures, explants, and transformed cells. A biological sample is typically obtained from a mammal, such as a primate, e.g., human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., prostate), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy," or a "fine-needle aspiration biopsy" which generally obtains a suspension of cells from within a target tissue. Biopsy techniques are discussed, for example, in Harrison's Principles of Internal Medicine (2005). Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) SGK1 expression. Representative pictures showing SGK1 expression is increased in prostate cancer cells compared to benign surrounding epithelium (1st panel-20x magnification, black line is drawn to show demarcation of cancerous area). In TN-PC (middle two panels) SGK1 expression is variable. In AD-PC, high SGK1 expression was less frequent (40x). (FIG. 1B) GR was expressed in a higher percentage of AD-PC compared to TN-PC (40x). (FIG. 1C) AR expression was universally positive and predominantly nuclear in both TN-PC and AD-PC (40x).

(FIG. 2C) Stratified by SGK1 expression high (3+) versus low (0 to 2+).

DETAILED DESCRIPTION OF THE INVENTION

Figures 1A, 1B, 1C:
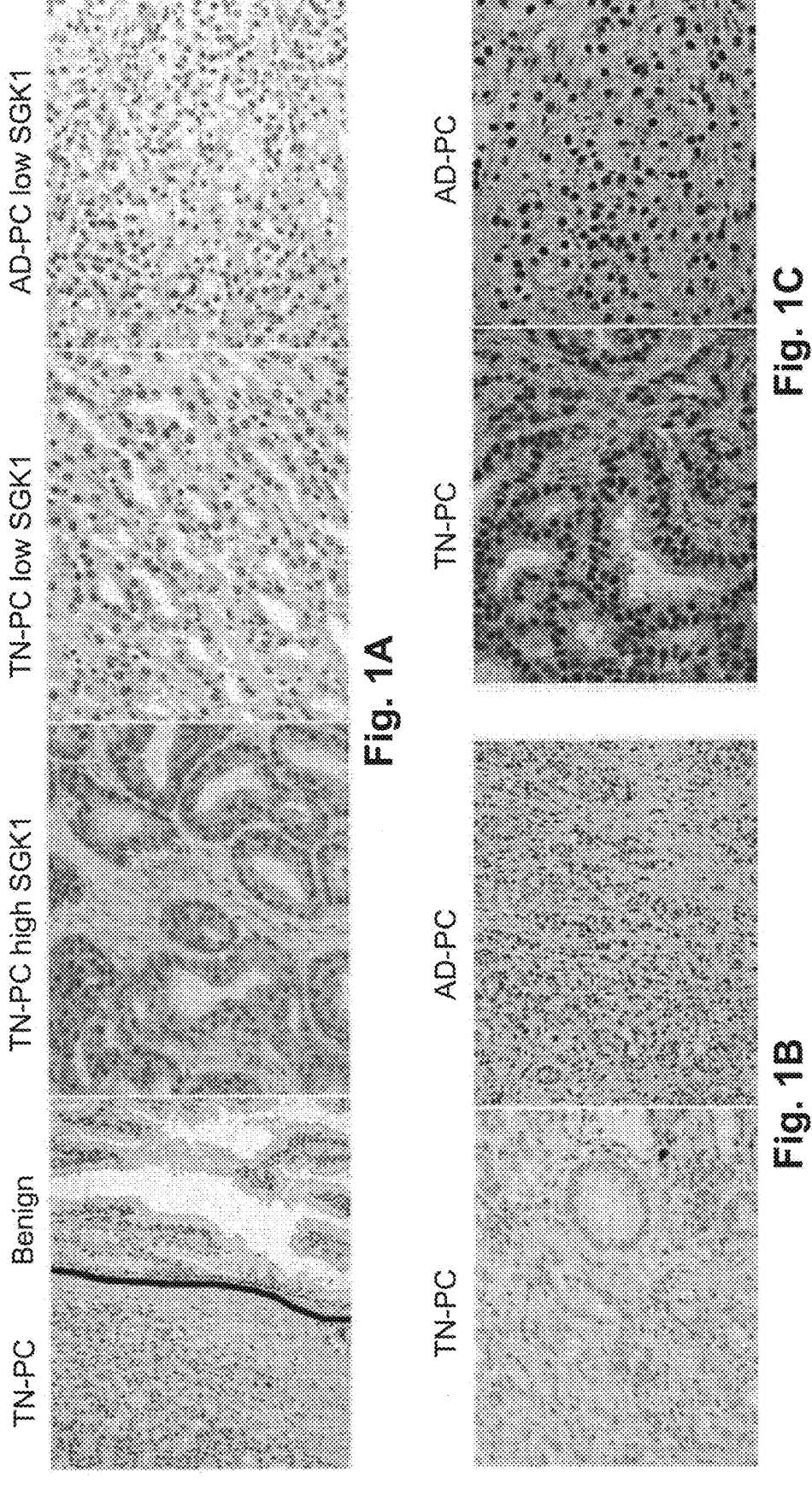
FIGS. 1A-C. Immunohistochemical analysis of prostate cancer tissue.

SGK1 has recently been identified as an AR-regulated target gene that encodes a protein kinase important in prostate cancer cell survival. Currently, there is a paucity of knowledge regarding SGK1 expression and its clinical significance in primary prostate cancers. The inventors examined the expression of SGK1 along with its nuclear receptor regulators AR and GR in both untreated and androgen-deprived human prostate cancer. They found that SGK1 is expressed in virtually all prostate cancers, but that the level of SGK1 expression is variable. SGK1 expression was consistently more intense in tumor epithelial cells compared to unaffected surrounding prostate tissue, supporting the notion that increased AR activity induces SGK1 expression. This observation contradicts a previous study examining SGK1 expression, which demonstrated a decrease in expression in tumor tissue samples when compared to benign prostatic hypertrophy (Rauhala et al., 2005). This difference may be due to the comparison of cancer to benign prostatic hypertrophy in the previous study, rather than a comparison to unaffected adjacent normal prostate tissue as in this study. Furthermore, the finding that SGK1 expression decreases following androgen-deprivation therapy supports the finding that SGK1 expression is AR-mediated.

Although only statistically significant at 5 years, it is nonetheless interesting that the inventors found an increased risk of prostate cancer recurrence in patients with lower SGK1 expression. This finding contradicted the inventors' initial hypothesis that high SGK1 expression in untreated primary prostate cancers would predict an increased risk of recurrence secondary to enhanced cancer cell survival. However, because SGK1 is an AR target gene, lower expression of SGK1 despite strong AR expression may reflect aberrant androgen pathway signaling associated with a less differentiated tumor phenotype. This hypothesis is consistent with the association between a higher Gleason grade and lower SGK1 expression found in this study. In support of this hypothesis, another study examining the expression of the AR target gene PSA/HK3 in prostate cancer found a similar inverse correlation between this AR-regulated gene and biochemical recurrence (Sterbis et al., 2008). On the other hand, a recent publication by Donovan et al. (2010) using a novel qualitative immunofluorescence scoring system for nuclear AR expression found an association of higher nuclear AR expression with increased prostate cancer specific mortality. Other studies examining AR (NR3C4) mRNA levels in primary tumor tissue also found an increase in biochemical relapse in patients with higher AR (NR3C4) mRNA compared to benign surrounding tissues (Rosner et al., 2007; Li et al., 2004). These findings likely reflect a difference between measurable AR expression and actual AR pathway activity reflecting the complexity of AR pathway signaling in prostate cancer biology. There are multiple possible mechanisms underlying potentially decreased AR signaling, even in the setting of intact testosterone. These are only now coming to light, and include AR splice variants and mutations (Guo et al., 2009; Koochekpour, 2010; Sun et al., 2010).

It is clear that this study has several limitations. Foremost is that the percentage of tumors with low SGK1 expression was only ~25% of the total sample size; analysis of this population is therefore limited. The second major limitation is that many patients were lost to follow-up over time. The wide range of follow-up from 6 weeks to over 15 years may confound the PFS analyses. In addition, several of the statistical associations between SGK1 expression and clinical parameters were suggestive of an association while not meeting the P≤0.05 cut-off, although the association with relapse at 5 years was statistically significant. A larger sample size, potentially enriched for patients with higher grade disease, would likely strengthen these findings. Furthermore, more consistent long-term follow-up would also potentially allow more robust statistical analyses to be made. Such studies, including multivariate analyses, receiver operating curves, and correlation coefficients would clearly be necessary to justify the use of SGK1 staining as a prognostic biomarker.

Although SGK1 is a known effector of the glucocorticoid pathway (Mikosz et al., 2001) and glucocorticoids are utilized in systemic therapy for castrate-resistant prostate cancer, little is known about either GR expression in prostate cancer or how glucocorticoids may be exerting a therapeutic effect. To the inventors' knowledge, there have only been two prior studies investigating GR expression in prostate cancer (Yemelyanov et al., 2007; Mohler et al., 1996). In line with previous GR expression data, the inventors have also found that GR was expressed in approximately a third of PC samples when compared to adjacent normal prostate tissue. Interestingly, this study demonstrates that GR is expressed in a higher proportion of androgen-deprived compared to treatment-naïve primary prostate cancer samples, which neither of the prior studies examined. Furthermore, of the five castrate-resistant samples from the AD-PC group, four overexpressed GR (80%). Although the sample size is small, this finding is interesting and could be explained by the fact that in an androgen-depleted environment, GR expression increases to compensate for decreased AR activity. AR and GR share similar DNA binding domain sequences as well as some of the same downstream effector genes, including SGK1 (Cleutjens et al., 1997; Ho et al., 1993; Chen et al., 1997). It is well known that the AR remains relevant in the progression to castrate-resistant prostate cancer (Zegarra-Moro et al., 2002; Scher and Sawyers, 2005). The inventors also considered it possible that in an androgen-depleted, castrate-resistant environment, GR might retain a role in transcriptional regulation of androgen-regulated genes such as SGK1, and could serve as a survival pathway for castrate-resistant prostate cancer. The inventors' observation that SGK1 expression remained high in nearly half of androgen-deprived cancers is consistent with this hypothesis.

Thus, in further studies, the inventors tested whether, following androgen-deprivation therapy (ADT) and the loss of AR activity in prostate cancer cells, administration of GR antagonists would have an effect. As shown herein, the inventors demonstrated that in the context of androgen receptor antagonism, the levels of glucocorticoid receptor (GR) within human castrate-resistant prostate cancer cell lines increases compared to those who have not been treated with AR inhibition, GR activation makes these castrate-resistant cell lines more resistant to AR inhibition, and that treatment of these cell lines with GR antagonists results in synergistic growth inhibition. These and other aspects of the invention are described in detail below.

I. PROSTATE CANCER

Prostate cancer is a form of cancer that develops in the prostate, a gland in the male reproductive system. Many prostate cancers are slow growing; however, it remains the leading cause of cancer death in men in the United States. (en.wikipedia.org/wiki/Prostate_cancer—cite_note-0). The cancer cells may metastasize (spread) from the prostate to other parts of the body, particularly the bones and lymph nodes. Prostate cancer may cause pain, difficulty in urinating, problems during sexual intercourse, or erectile dysfunction. Other symptoms can potentially develop during later stages of the disease.

Rates of detection of prostate cancers vary widely across the world, with South and East Asia detecting less frequently than in Europe, and especially the United States. Prostate cancer tends to develop in men over the age of fifty and although it is one of the most prevalent types of cancer in men, many never have symptoms, undergo no therapy, and eventually die of other causes. This is because cancer of the prostate is, in most cases, slow-growing, symptom-free, and since men with the condition are older they often die of causes unrelated to the prostate cancer, such as heart/circulatory disease, pneumonia, other unconnected cancers, or old age. On the other hand, the more aggressive prostate cancers account for more cancer-related mortality than any other cancer except lung cancer. About two-thirds of cases are slow growing, the other third more aggressive and fast developing.

Many factors, including genetics and diet, have been implicated in the development of prostate cancer. The presence of prostate cancer may be indicated by symptoms, physical examination, prostate-specific antigen (PSA), or biopsy. The PSA test increases cancer detection but does not decrease mortality (en.wikipedia.org/wiki/Prostate_cancer-cite_note-BMJ2010-4). Moreover, prostate test screening is controversial at the moment and may lead to unnecessary, even harmful, consequences in some patients. Nonetheless, suspected prostate cancer is typically confirmed by taking a biopsy of the prostate and examining it under a microscope. Further tests, such as CT scans and bone scans, may be performed to determine whether prostate cancer has spread.

Management strategies for prostate cancer should be guided by the severity of the disease. Many low-risk tumors can be safely followed with active surveillance. Curative treatment generally involves surgery, various forms of radiation therapy, or, less commonly, cryosurgery; hormonal therapy and chemotherapy are generally reserved for cases of advanced disease (although hormonal therapy may be given with radiation in some cases).

The age and underlying health of the man, the extent of metastasis, appearance under the microscope and response of the cancer to initial treatment are important in determining the outcome of the disease. The decision whether or not to treat localized prostate cancer (a tumor that is contained within the prostate) with curative intent is a patient trade-off between the expected beneficial and harmful effects in terms of patient survival and quality of life.

Early prostate cancer usually causes no symptoms. Sometimes, however, prostate cancer does cause symptoms, often similar to those of other prostate diseases such as benign prostatic hyperplasia. These include frequent urination, nocturia (increased urination at night), difficulty starting and maintaining a steady stream of urine, hematuria (blood in the urine), and dysuria (painful urination).

Prostate cancer is associated with urinary dysfunction as the prostate gland surrounds the prostatic urethra. Changes within the gland, therefore, directly affect urinary function. Because the vas deferens deposits seminal fluid into the prostatic urethra, and secretions from the prostate gland itself are included in semen content, prostate cancer may also cause problems with sexual function and performance, such as difficulty achieving erection or painful ejaculation.

Advanced prostate cancer can spread to other parts of the body, possibly causing additional symptoms. The most common symptom is bone pain, often in the vertebrae (bones of the spine), pelvis, or ribs. Spread of cancer into other bones such as the femur is usually to the proximal part of the bone. Prostate cancer in the spine can also compress the spinal cord, causing leg weakness and urinary and fecal incontinence.

The only test that can fully confirm the diagnosis of prostate cancer is a biopsy, the removal of small pieces of the prostate for microscopic examination. However, prior to a biopsy, less invasive testing can be conducted. There are several tests that can be used to gather more information about the prostate and the urinary tract. Digital rectal examination (DRE) may allow a doctor to detect prostate abnormalities. Cystoscopy shows the urinary tract from inside the bladder, using a thin, flexible camera tube inserted down the urethra. Transrectal ultrasonography creates a picture of the prostate using sound waves from a probe in the rectum. PSA level tests also are used frequently to screen for higher risk patients.

Prostate cancer is initially "hormone dependent", meaning its growth and progression is dependent on androgen hormones. The majority of these hormones are produced by the testicles. Most hormone dependent cancers become refractory after one to three years and resume growth despite hormone therapy. Previously considered "hormone-refractory prostate cancer" or "androgen-independent prostate cancer," the term "castration-resistant" has replaced "hormone refractory" because while they are no longer responsive to castration treatment (reduction of available androgen/testosterone/DHT by chemical or surgical means), these cancers still show reliance upon hormones for androgen receptor activation. Before 2004, all treatments for castration-resistant prostate cancer (CRPC) were considered palliative and not shown to prolong survival. However, there are now several treatments available to treat CRPC that improve survival.

The cancer chemotherapeutic docetaxel has been used as treatment for CRPC with a median survival benefit of 2 to 3 months. Docetaxel's FDA approval in 2004 was significant as it was the first treatment proven to prolong survival in CRPC. In 2010, the FDA approved a second-line chemotherapy treatment known as cabazitaxel. Off-label use of the oral drug ketoconazole is sometimes used as a way to further manipulate hormones with a therapeutic effect in CRPC. However, many side effects are possible with this drug and abiraterone is likely to supplant usage since it has a similar mechanism of action with less toxic side effects. The immunotherapy treatment with sipuleucel-T is also effective in the treatment of CRPC with a median survival benefit of 4.1 months.

The second line hormonal therapy abiraterone (Zytiga) completed a phase 3 trial for CRPC patients who have failed chemotherapy in 2010. Results were positive with overall survival increased by 4.6 months when compared to placebo. On Apr. 28, 2011, the U.S. Food and Drug Administration approved abiraterone acetate in combination with prednisone to treat patients with late-stage (metastatic) castration-resistant prostate cancer patients who have received prior docetaxel (chemotherapy). Another anti-androgen pathway therapy, MDV3100, is an extremely potent and specific inhibitor of the androgen receptor. A phase III clinical trial of MDV3100 in castration-resistant prostate cancer patients who have received prior docetaxel (chemotherapy) was reported in 2012, and similarly demonstrated a 4-5 month survival advantage. It has yet to be approved by the FDA, however its approval is likely.

II. GLUCOCORTOCOID AND ANDROGEN RECEPTOR ANTAGONISTS

A. Glucocortocoid Receptor Antagonists

Early research on steroidal ligands led to the identification of the non-selective GR antagonist RU-486 (mifepristone) and the GR-selective steroid RU-43044. Others include dual antagonist-agonists beclometasone, betamethasone, budesonide, ciclesonide, flunisolide, fluticasone, mometasone, and triamcinolone. Structurally-related compounds that also are GR antagonists include octahydrophenanthrenes, spirocyclic dihydropyridines, triphenylmethanes and diaryl ethers, chromenes, dibenzyl anilines, dihydroisoquinolines, pyrimidinediones, azadecalins, aryl pyrazolo azadecalins, 11-monoaryl steroids, phenanthrenes, dibenzol [2.2.2]cycloctaines and derivatives, dibenzoclyclohepatnes and their derivatives, dibenzyl anilinesulfonamides and their derivatives, dihetero(aryl) pentanol, chromene derivatives, Azadecalins, aryl quinolones, 11,21-bisaryl steroids and 11-aryl, and 16-hydroxy steroids. Collectively, these compounds are referred to herein as "GR antagonists." See Moeler et al., *Expert Opin.*, 17 (1), 2007).

B. Androgen Receptor Antagonists

Cyproterone Acetate. Cyproterone acetate is a progestional anti-androgen that directly inhibits the androgen receptor. Co-cyprindol combines (COCs) 2 mg CPA with 35 ethinyl estradiol and it has been suggested that the higher amount of estrogen in these agents carries a greater potential for VTE compared with conventional lower estrogen-containing COCs. However, evidence for adverse effects of co-cyprindol concerning higher VTE risk suggests it is no greater than with third-generation COCs. Cyproterone is no longer in used in the United States.

Spironalactone. Spironalactone has inhibitory actions on both the androgen receptor and 5α-reductase. Spironalactone is not without side effects, although these are largely dose dependent. Potential hyperkalemia, fatigue, headache, fluid retention and, rarely, melasma have been observed. Animal studies have reported an association with breast carcinoma in rodents but this has not been replicated in human studies. All patients should undergo regular monitoring of their electrolytes owing to the potassium-retaining effects on the kidney.

Flutamide. Flutamide is a nonsteroidal potent androgen antagonist, most routinely used in the treatment of prostate cancer. In terms of safety, fatal hepatotoxicity has been reported with flutamide. Initial warnings of hepatotoxicity were reported from patients using doses of 750 mg daily and reported prior to any dose-response studies being undertaken. The use of lower doses of flutamide is currently under investigation. No cases of hepatic impairment with flutamide doses of 125 mg/day or less have been reported, and placebo-controlled data suggest that doses as low as 250-375 mg/day may be effective in antagonizing androgen production in females, especially when combined with a drospirenone-containing contraceptive.

Bicalutamide. Bicalutamide (marketed as Casodex, Cosudex, Calutide, Kalumid) is an oral non-steroidal anti-androgen used in the treatment of prostate cancer and hirsutism. It is recommended 50 mg once daily in combination with a luteinizing hormone-releasing hormone analogue or surgical castration or upon progression after castration as a secondary hormonal maneuver.

Nilutamide. Nilutamide is an antiandrogen medication used in the treatment of advanced stage prostate cancer. Nilutamide blocks the androgen receptor, preventing its interaction with testosterone. Because most prostate cancer cells rely on the stimulation of the androgen receptor for growth and survival, nilutamide can prolong life in men with prostate cancer. Nilutamide is marketed under the name Nilandron in the United States and under the name Anandron in Canada. It is used in combination with a luteinizing hormone-releasing hormone analogue or surgical castration or upon progression after castration as a secondary hormonal maneuver.

MDV3100. MDV3100 is an experimental androgen receptor antagonist drug developed by Medivation for the treatment of castration-resistant prostate cancer currently in Phase 3 clinical trials. Medivation has reported up to an 89% decrease in prostate specific antigen serum levels after a month of taking the medicine. Early preclinical studies also suggest that MDV3100 inhibits breast cancer cell growth.

MDV3100 has approximately five-fold higher binding affinity for the androgen receptor (AR) compared to the antiandrogen bicalutamide. As opposed to bicalutamide, MDV3100 does not promote translocation of AR to the nucleus and in addition prevents binding of AR to DNA and AR to coactivator proteins. When LNCaP cells (a prostate cancer cell line) engineered to express elevated levels of AR (as found in patients with advanced prostate cancer) were treated with MDV3100, the expression of androgen dependent genes PSA and TMPRSS2 were down regulated in contrast to bicalutamide where the expression was upregulated. In VCaP cells which over express androgen receptors, MDV3100 induced apoptosis, whereas bicalutamide did not. Furthermore MDV3100 behaves as an antagonist of the W741C mutant androgen receptor in contrast to bicalutamide which behaves as a pure agonist when bound to the W741C mutant.

MDV 3100 was found clinically active for metastatic castration-resistant prostate cancer patients in ongoing phase I and II trials. PSA level decreased more than 50 percent in 40/65 chemo-naive patients and 38/75 chemotherapy-treated patients. Recent long-term follow up data from these early clinical studies, announced in February 2011, were positive. Median time to radiographic progression was 56 weeks for chemo-naive patients and 25 weeks for the post-chemotherapy population. Medivation is conducting several international phase III trials. The first trial, known as AFFIRM, will determine the effectiveness of MDV3100 in patients who have previously failed chemotherapy treatment with docetaxel. In November 2011, this trial was halted after an interim analysis revealed that patients given the drug lived for approximately 5 months longer than those taking placebo. As noted above, these preliminary reports were reported to the public in early 2012. Medivation is expected to file for FDA approval sometime in 2012.

There is another phase III trial, known as PREVAIL, that is investigating the effectiveness of MDV3100 with patients who have not yet received chemotherapy. As of October 2011, this trial is still open to accrual. In addition, a phase II trial began in March 2011 comparing MDV3100 with a commonly used anti-androgen, bicalutamide, in prostate cancer patients who have progressed while on LHRH analogue therapy (e.g., leuprorelin) or surgical castration.

III. PROSTATE CANCER THERAPY

Classically, metastatic prostate cancer is treated with first line androgen deprivation therapy (ADT). ADT lowers serum testosterone, the hormone that drives proliferation and progression of the disease through activation of the androgen receptor (AR) within the cancer cell. Patients respond to ADT for a finite duration, on average 2-3 years, after which, they are considered to have failed first line hormonal therapy and are considered to have castration resistant prostate cancer (CRPC). CRPC is the lethal form of the disease, causing over 30,000 deaths in the United States alone.

The decapeptide gonadotropin-releasing hormone, also referred to as LHRH, was isolated in 1971. Chronic exposure to LHRH ultimately suppressed testosterone by desensitizing pituitary cells through downregulation of the LHRH receptors. Substitutions at the sixth amino acid position of LHRH resulted in significantly more potent LHRH agonists. The monthly depot of leuprolide was the first LHRH agonist evaluated as a treatment for advanced prostate cancer. In a randomized clinical trial, leuprolide was equivalent to 3 mg of DES in reducing serum testosterone to castrate levels. The advantage of leuprolide was a lower incidence of cardiovascular toxicity. Leuprolide ultimately replaced DES and orchiectomy as the preferred approach to androgen deprivation.

Over the next 30 years, substitutions at the sixth amino acid position yielded goserelin, triptorelin, and histrelin, which are the commercially available LHRH agonists in the United States. LHRH agonists are differentiated by their route of administration (intramuscular injection vs subcutaneous injection vs subcutaneous implant) and frequency of administration (1-12 months). All of these LHRH agonists seem to have similar side effect profiles and the ability to lower serum testosterone to castrate levels. There has only been 1 study directly comparing different LHRH agonists. Overall survival was significantly greater with triptorelin compared with leuprolide, 97% vs 90.5% survival at 9 months, respectively (P=0.033). Although not statistically significant, there was a trend for triptorelin to better maintain castrate levels of testosterone over a 9-month interval.

One of the paradigm changing discoveries in the management of CRPC is that despite having progressed despite ADT, CRPC remains in large part driven by active androgen receptor signaling. This has led to the development of therapies targeting the androgen axis including abiraterone (De Bono et al., 2011), which decreases the production of other ligands similar in function to testosterone, and most recently MDV3100, a second generation, potent inhibitor of the androgen receptor. Although MDV3100 improves survival, its benefits are limited, with the median duration of benefit (progression free survival in the pivotal phase III trial) of just over 8 months. After progression on MDV3100 the median survival is under 1 year, and it is unclear how the prostate cancer becomes resistant to MDV3100 and similar potent AR inhibitors.

According to the present invention, prostate cancers resistant to AR inhibition can now be treated with GR antagonists. Thus, it is specifically contemplated that one or more of the GR antagonists discussed herein or in the incorporated references may be used in the treatment of prostate cancer, and in particular, CRPC. It is also contemplated that in some embodiments, more than one GR antagonist is employed, while in other embodiments, only one is employed as part of the therapeutic method (though it may be administered multiple times). It is contemplated that the second one may be administered concurrently with the first one or they may be administered at different times.

Moreover, GR antagonist therapies may be combined, advantageously, with conventional cancer therapies. These include one or more selected from the group of chemical or radiation based treatments and surgery. Chemotherapies include, for example, cisplatin (CDDP), carboplatin, cabazitaxel, mitoxantrone, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against prostate cancer. These prostate cancer chemotherapeutics are capecitabine, carboplatin, cyclophosphamide (Cytoxan), cabazitaxel, daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thio-colchicine derivative and a carrier protein (such as albumin).

In further embodiments, a combination of chemotherapeutic agents is administered to prostate cancer cells. The chemotherapeutic agents may be administered serially (within minutes, hours, or days of each other) or in parallel; they also may be administered to the patient in a pre-mixed single composition. The composition may or may not contain a glucocorticoid receptor antagonist. Combinations of prostate cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol).

The term "a serine/threonine kinase inhibitor," as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-κB, eIF2α, COX2, RANTES, IL8, CYP2A5, IGF-1, CYP2B1, CYP2B2, CYP2H1, ALAS-1, HIF-1, erythropoietin and/or CYP1A1. An example of a serine/threonine kinase inhibitor includes, but is not limited to, Sorafenib and 2-aminopurine, also known as 1H-purin-2-amine(9CI). Sorafenib is marketed as NEXAVAR. The compounds can be used in combination with a glucocorticoid receptor antagonist.

The term "an angiogenesis inhibitor," as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCLS, TGF-0, lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R,4S,5S, 6R)-5-methoxy-4-[(2R,3R)-2-methyl-3-(3-methyl-2-butenyl)oxi-ranyl]-1-oxaspiro[2.5]oct-6-yl]ester, (2E,4E,6E, 8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID. The compounds can be used in combination with a glucocorticoid receptor antagonist.

Radiation therapies that cause DNA damage and have been used extensively include what are commonly known as $\gamma$-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. In particular, intravenous administration of samarium, strontium and radium-223 are contemplated.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems. Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16, FHIT and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Various combinations with a glucocorticoid receptor antagonist and an anticancer agent or compound (or a combination of such agents and/or compounds) may be employed, for example glucocorticoid receptor antagonist is "A" and the conventional anticancer therapy or agent (or a combination of such agents) given as part of an anticancer therapy regime, is "B":

A/B/A B/A/B B/B/A A/A/B A/B/B B/A/A A/B/B/B B/A/B/B B/B/B/A
B/B/A/B A/A/B/B A/B/A/B A/B/B/A B/B/A/A B/A/A/B
B/A/B/A A/A/A/B B/A/A/A A/B/A/A A/A/B/A

Administration of the therapy or agents to a patient will follow general protocols for the treatment/administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The terms "contacted" and "exposed," when applied to a cell, are used herein to describe the process by which a GR antagonist and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue. Upon excision of part of all of cancerous cells, tissue, or tumor, a cavity may be formed in the body. Treatment may be accomplished by perfusion, direct injection or local application of the area with or without an additional anticancer therapy.

Other aspects of therapy include assessing AR or GR expression or activity. Methods for assessing the level of expression or activity of these receptors is described in greater detail in U.S. Patent Publication No. 2011/0269728, the entire contents of which are hereby incorporated by reference.

IV. PHARMACEUTICAL FORMULATIONS, ROUTES OF ADMINISTRATION AND KITS

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, to tumor vasculature or in a resected tumor bed.

Treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of GR antagonist described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single GR antagonist or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Ed., 1990). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Kits may provided with one or more agents according to the present invention, for example, in the form of a container with a label. Suitable containers include, for example, bottles, vials, and test tubes. The containers may be formed from a variety of materials such as glass or plastic. The label on the container may indicate that the composition is used for a specific prognostic or therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1—Materials and Methods

Human Tissue Procurement. Tissue microarrays were constructed by the Human Tissue Research Center at the University of Chicago Medical Center with Institutional Review Board approval. As described previously, a nested case control was used to select 138 prostate cancer samples from over 500 consecutive radical prostatectomies performed at the University of Chicago between 1995 and 2002 for the tissue microarray used in this study (Lotan et al., 2007). Areas involved by prostate cancer and adjacent non-neoplastic prostatic tissue were punched (2 mm cores) from the formalin-fixed, paraffin embedded samples and arrayed with 72-108 cores per slide. These tissues are referred to as "treatment-naive prostate cancer" (TN-PC). Of this total (excluding duplicates), 126 samples had a reported Gleason grade, 125 had available staging data, and 122 had an associated preoperative PSA. In addition, 18 full tissue sections of prostate cancer following hormonal treatment (androgen deprivation±anti-androgen or anti-androgen receptor therapy) were cut into 4 µm sections, mounted on slides for immunohistochemistry staining. These samples are referred to as "androgen-deprived prostate cancer" (AD-PC). These 18 samples included prostate cancer tissue samples from 10 radical prostatectomies after preoperative androgen deprivation, 6 transurethral prostatectomies, 1 pelvic exenteration, and 1 femoral head biopsy with metastatic prostate cancer. Five of these 18 full sections were samples from bona fide "castrate-resistant" prostate cancers in that the samples were from patients with progression of disease despite pharmacologic or surgical castration. Patient age ranged between 42 and 93 years (42-81 for treatment-naive and 48-93 for androgen-deprived patients), with a median age of 63 years, and a mean age of 62.4 years. Patient disease characteristics including grade, stage and PSA are detailed in Table I. The majority of both treatment-naive and androgen-deprived samples had a Gleason grade between 6 and 7 (75% and 67%, respectively). The majority of prostatectomy samples were organ-confined as pathologic stage T2 (56%). Twenty-eight patients (20%) had extra-capsular extension, and another 23 patients (17%) were not organ-confined because of seminal vesicle invasion, invasion of bladder/rectum, nodal involvement, or bone metastasis at the time of surgery.

TABLE 1

Prostate Cancer Tumor Characteristics

| | Treatment-naïve | Androgen-deprived |
|---|---|---|
| Gleason grade number (%) | | |
| 5 | 23 (18.2) | 3 (16.7) |
| 6 | 35 (27.8) | 3 (16.7) |
| 7 | 60 (47.6) | 9 (50) |
| 8-9 | 8 (6.4) | 3 (16.7) |
| Pathologic stage number (%) | | |
| T2aN0 | 7 (5.6) | |
| T2bN0 | 11 (8.8) | |
| T2cN0 | 58 (46.4) | |
| T2cN1 | 1 (0.8) | |
| T3aN0 | 27 (21.6) | |
| T3aN1 | 3 (2.4) | |
| T3bN0 | 12 (9.6) | |
| T3bN1 | 3 (2.4) | |
| T4 | 3 (2.4) | |
| PSA | | |
| Mean (±standard deviation) | 9.0 (7.35) | |
| Median (range) | 6.75 (3.3-43.8) | |

Immunohistochemistry. Immunohistochemical stains for androgen (AR) and GR as well as SGK1 were performed as previously described (Sahoo et al., 2005; Niemeier et al., 2010; Belova et al., 2009). Briefly, slides were covered with xylene for a total of 10 min, then immersed in ethanol of decreasing dilutions (100% ethanol to 70% ethanol) and washed with Tris-buffered saline (TBST) for 2 min. Antigens were unmasked with sodium citrate buffer pH 6.0 followed by heat treatment at 95° C. After cooling, slides were placed in 3% hydrogen peroxide for 20 min and then washed in TBST. Next, to block endogenous peroxidase and protein, slides were incubated in the dark in a milk-peroxide solution (90 parts $dH_2O$, 5 parts skim milk, and 5 parts 3% hydrogen peroxide) and then again washed in TBST. The primary antibody, in blocking buffer, was then applied to the slide. The slides were incubated with the primary antibody for 30 min and then washed. After application of the primary antibody, the DAKO EnVision+ System-HRP (DAB (3,3'-diaminobenzidine)) was used. Omitting the primary antibody step served as a negative control for all tissues. The following antibodies were used: anti-AR (AR441 1:50, Dako), anti-GR (NCLGCR 1:20, Novocastra), and anti-SGK1 (1:150, Affinity Bioreagents, C Terminal SGK1 antibody). All antibodies were assessed semi-quantitatively in both prostate cancer and adjacent non-neoplastic prostatic tissue. Any nuclear and/or cytoplasmic immunoreactivity was recorded. Intensity was graded on a four-point scale from 0 to 3 to represent negative, weak, moderate, and strong, respectively. This scoring was performed by two pathologists who reviewed the immunoreactivity together and arrived at a consensus score that was used in the analyses.

Follow-Up and Cancer Recurrence Analysis. Follow-up data were collected using the University of Chicago Prostate Cancer Database (UCPC). All patients undergoing surgery, in this case radical prostatectomy, are captured in the electronic UCPC Database. The database contains detailed demographic, surgical, pathological, functional as well as long-term oncologic outcome data. The follow-up and outcome data were collected using surveys (mail, e-mail, and phone) at, 3, 6, 12, and 24 months after surgery and annually thereafter. Professional support by the Survey Lab at University of Chicago was utilized. Oncologic outcome was confirmed by mailed/emailed/faxed tumor marker (PSA) results, reports for adjuvant treatments as well as queries to death registries. For prostate cancer recurrence analysis, PSA recurrence post-prostatectomy was defined as any PSA value above the lower limits of detection. Patients whose PSA failed to nadir to undetectable post-prostatectomy were considered to have met the recurrence endpoint at the date of first PSA follow-up. Patients were censored from the analysis at the time of last follow-up if they were alive and had not met criteria for PSA recurrence. Time to PSA progression was calculated for groups based on Gleason grade and stage. Gleason scores 5 and 6 were considered low grade and were combined for this analysis. Similarly the Gleason scores 7, 8, and 9 were grouped as they represent more aggressive biology. Although it has been reported that Gleason sum 4+3 versus 3+4 cancers behave differently, many of the pathology reports available from this tissue set did not differentiate between the two, but rather listed the cancer as "Gleason 7." Thus, the group was analyzed together (Chan et al., 2000; Wright et al., 2009).

Statistical Analysis. Data were summarized using descriptive statistics. Fisher's exact test was used to compare categorical variables (e.g., high vs. low staining levels) between groups. The Kaplan and Meier method was used to estimate progression-free survival (PFS). Univariate analyses comparing PFS between groups were performed using the log-rank test. In addition, the Wilcoxon-Breslow-Gehan log-rank test, which gives higher weight to the earlier data points, was used to compare PFS between SGK-1 expression groups. Univariate Cox proportional hazards regression models were used to estimate hazard ratios between groups. PFS rates at 2 and 5 years were compared using a chi-squared test with a complementary log-log transformation of the Kaplan-Meier estimator (Klein et al., 2007).

GR Antagonist Studies. CWR-22RV1 (22RV1) and LAPC4 prostate cancer cell lines were grown in vitro with various combinations of the AR antagonist MDV3100 (10 µM), synthetic androgen R1881 (10 nM), GR agonist dexamethasone (Dex, 1 µM or 100 nM, the GR inhibitor mifepristone (Mif, 100 nM), or the SGK1 kinase inhibitor GSK650394 (1 µM). SGK1-FLAG or vector was stably expressed and cellular viability, secreted PSA, and protein lysates were collected.

Example 2

Immunohistochemistry of SGK1, GR, and AR Expression. AR and SGK1 were expressed in essentially all prostate epithelium including TN-PC, AD-PC, and unaffected adjacent prostate tissue (UPT). As expected, nuclear AR expression was uniformly strong (3+) in all prostate cancer tissue samples regardless of treatment status (Table II, FIGS. 1A-C). SGK1 expression was consistently more intense in the prostate cancer samples compared to UPT (FIGS. 1A-C). Additionally, SGK1 expression was more intense in the nucleus versus the cytoplasm. As SGK1 expression by immunohistochemistry was strong in the majority of specimens, the four-point scale for SGK1 expression was grouped as high (3+) versus low (0, 1, and 2+) for further analysis. With this classification, 100 of 126 (79%) TN-PC samples were strongly positive for SGK1 compared to only 8 out of 18 (44%) AD-PC samples (P ¼ 0.003) (Table II, FIGS. 1A-C). There was no association between SGK1 expression and tumor stage. The percentage of patients with a low Gleason score (Gleason sum 5 or 6) and low SGK1 expression was nearly half of that compared to the percentage of high Gleason grade (7-9) tumors with low SGK1 expression (13.8% vs. 26.5%, P ¼ 0.08). This implies that SGK1 expression may inversely correlate with prostate tumor grade.

TABLE 2

IHCExpression of SGK1, AR, and GR

|  | SGK1 3+ (%)* (n = 126) | AR+ (%) (n = 126) | GR+ (%)** (n = 126) |
|---|---|---|---|
| TN-PC | 100 (79) | 126 (100) | 43 (38) |
| AD-PC | 8 (44) | 18 (100) | 14 (78) |

*P = 0.003, **P = 0.002 (Fisher's exact test).

The inventors next examined GR expression. Unlike AR, which was universally strongly positive regardless of whether the patient was untreated or androgen-deprived, GR expression was more variable. Specifically, GR expression was present in a significantly higher proportion of AD-PC compared to TN-PC (78% vs. 38% positive staining, P ¼ 0.002) (Table II, FIGS. 1A-C). Interestingly GR was highly expressed in four of five castrate-resistant AD-PC samples (80%), suggesting that increased GR activity may contribute to castration-resistance by bypassing AR blockade.

Figure 2A:
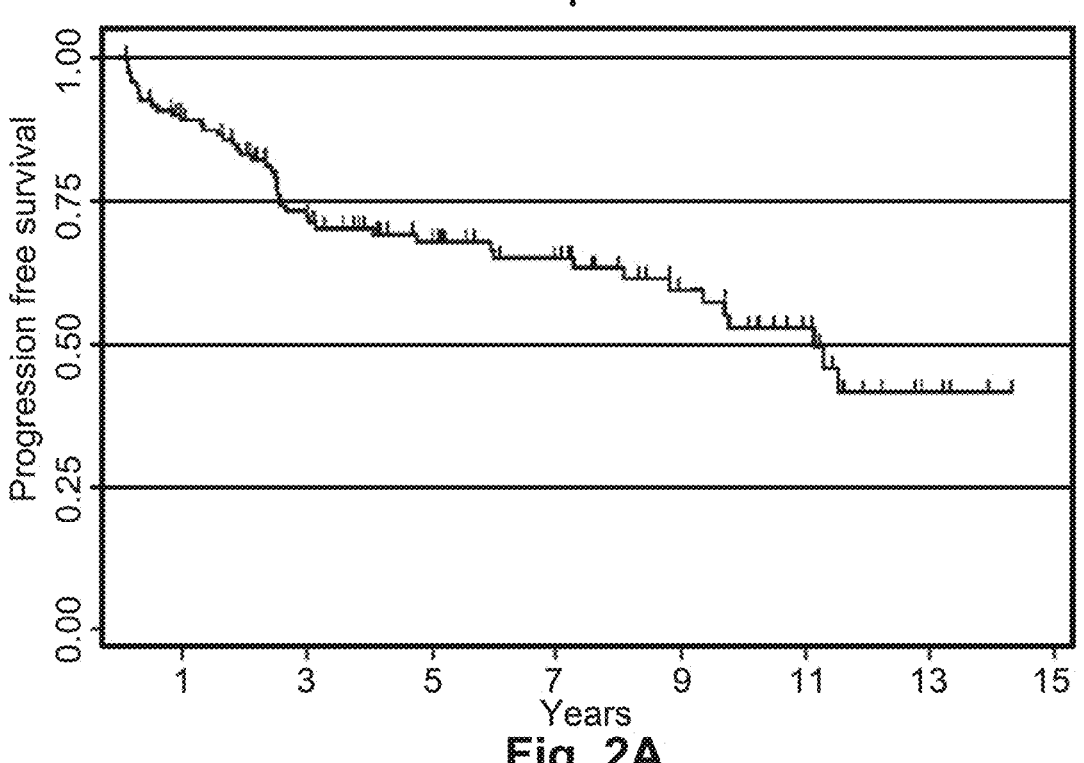
FIGS. 2A-C. PSA progression free survival estimates. Kaplan-Meier log-rank survival estimates of progression-free survival for (FIG. 2A). All patients (FIG. 2B). Stratified by Gleason grade low (5-6) versus intermediate/high (7-9).
Figure 2B:
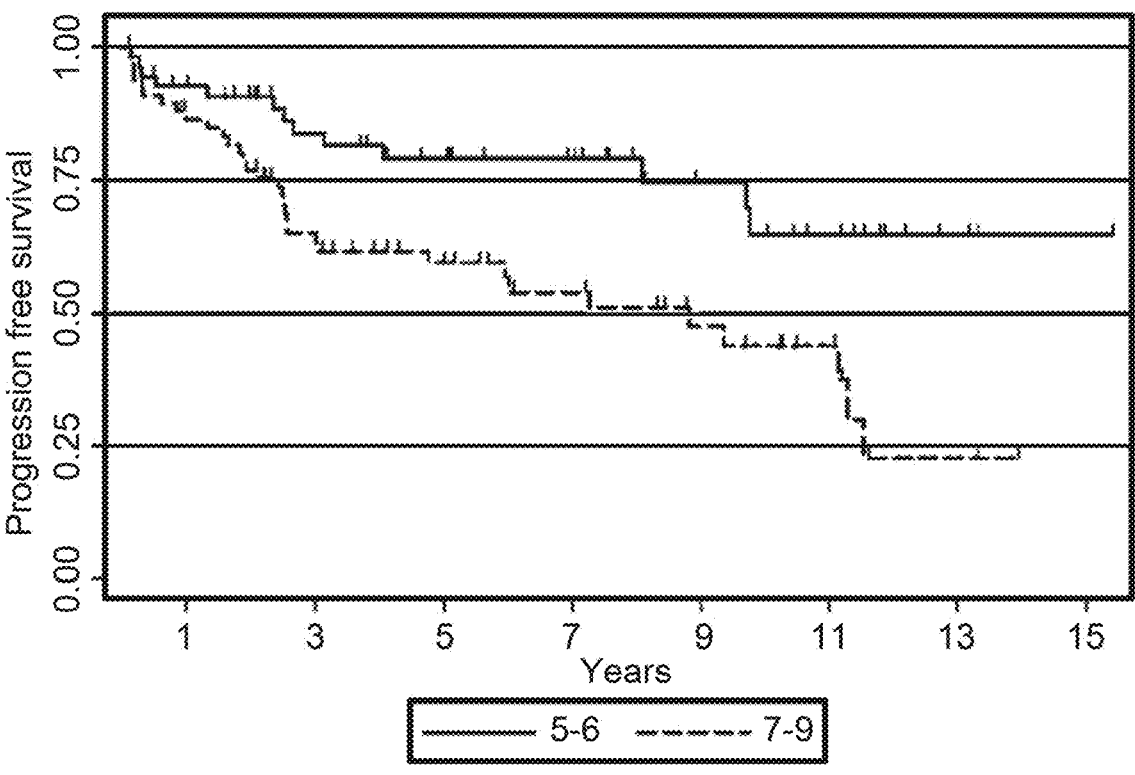
Figure 2C:
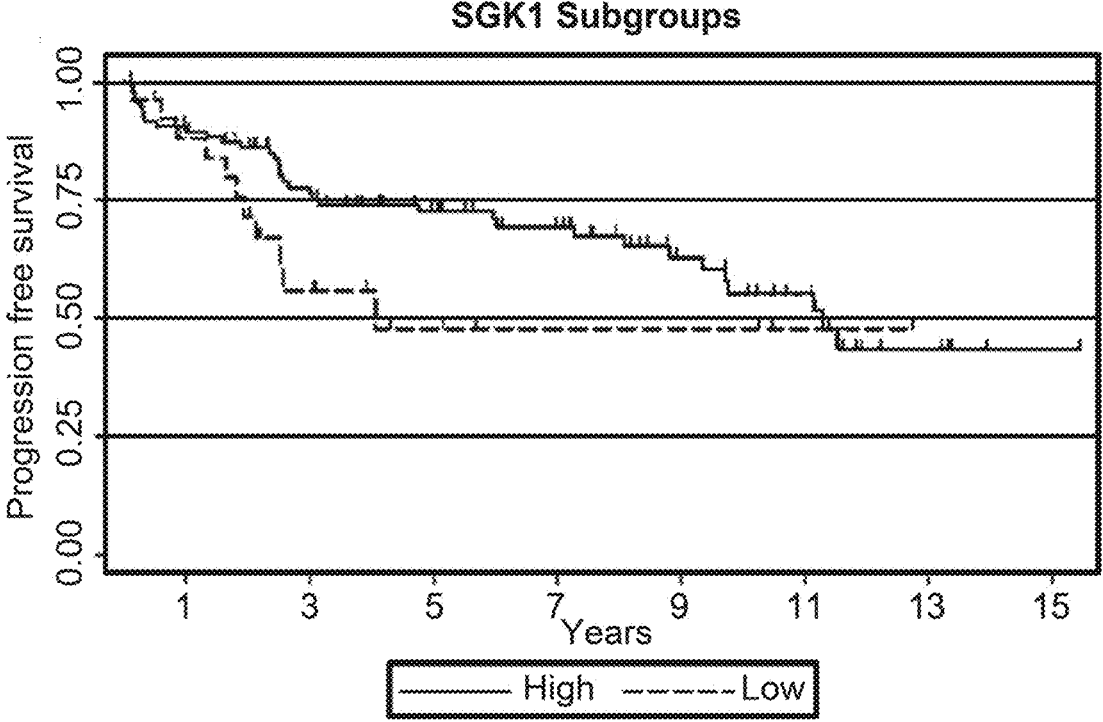

SGK1 Expression and Prostate Cancer Recurrence. To date, of the 122 TN-PC patients for whom there is follow-up data available, PSA recurrence post-prostatectomy has occurred in 37.7% (n=46). Of the 76 patients who have not met PSA recurrence criteria, the median follow-up is 5.5 years (range 0.11-15.4 years). The median progression-free survival [(PFS)=time from prostatectomy to PSA recurrence] for the entire cohort is 11.13 years (95% CI: 8.8—not reached) (FIG. 2A). Time to PSA progression was also calculated for patient subgroups based on tumor Gleason grade and stage. As expected, there was a statistically significant difference in PFS between the "low" and "high" Gleason grade subgroups (P=0.004) (FIG. 2B), and patients with high Gleason scores were at a higher risk of progression (HR=2.51) on univariate analysis. Higher tumor stage was similarly associated with an increased risk of relapse (P<0.0001). Overall, there was a non-statistically significant trend towards decreased PFS (worse outcome) associated with low (0 to 2+) SGK1 expression compared to high SGK1 expression (log-rank P=0.116; Wilcoxon-Gehan-Breslow log-rank test P=0.077) (FIG. 2C). At 2 years, 86.2% (95% CI: 77.3-91.7%) of patients were alive without progression in the high SGK1 group versus only 71.4% (95% CI: 49.1-85.2%) alive without progression in the low SGK1-expression group (P=0.083). At 5 years of follow-up, the percentage of patients without progression in the high SGK1 group was 72.6% (95% CI: 61.8-80.8%) versus only 47.8% (24.1-68.2%) in the low SGK1 group (P=0.034). These data support the hypothesis that low SGK1 expression in primary prostate tumors is associated with a worse clinical outcome compared to high SGK1 expression. This study provides strong supporting translational evidence from patient-derived prostate tissue that AR signaling regulates SGK1 expression in prostate cancer. Interestingly, there is a suggestion that SGK1 expression is inversely associated with grade and cancer recurrence. It is possible that aberrant AR signaling is associated with a poorly differentiated phenotype and unfavorable outcome. Following androgen deprivation, GR expression increases and SGK1 expression remains high in a subset of patients. Further study is needed to clarify the role of the AR/GR/SGK1 network in castration resistance. This study highlights an interesting interaction between AR signaling, SGK1, and GR in prostate cancer.

GR Antagonist Studies. Sustained androgen receptor (AR) signaling is required for the development of castrate resistant prostate cancer (CRPC). As shown above, following androgen deprivation therapy for prostate cancer, tumor glucocorticoid receptor (GR) expression is increased. The GR and AR are known to share similar DNA binding sequences and to regulate several common target genes, including the anti-apoptotic protein serum/glucocorticoid regulated kinase 1 (SGK1). The inventors hypothesized that increased GR expression might compensate for diminished AR signaling, thereby facilitating resistance to potent inhibitors of the AR through sustained expression of apoptosis inhibitor. Following MDV3100 treatment, GR expression increased in both CWR-22RV1 and LAPC4 cell lines. Although proliferation rates of both SGK1 and vector expressing cell lines were slower following Dex, there was a relative protection from MDV3100-associated cell death. For LAPC4 cells, cell survival compared to R1881 control was improved with Dex (66% vs. 47%, p<0.05). For 22RV1, Dex treatment also increased cell survival despite MDV3100 (151% vs. 51% without Dex). Dex treatment also led to increased PSA secretion despite MDV3100 treatment. For LAPC4 cells, secreted PSA levels (ng/nL) were 22.7 (R1881), 1.4 (MDV3100), and 31.5 (MDV3100+Dex). For the CWR-22RV1's there was similar antagonism of MDV3100 activity following Dex treatment: 10.9, 4.4, and 41.9 for R1881, MDV3100 and MDV3100+Dex respectively. Expression of SGK1 was reduced with MDV3100, but increased with the addition of Dex. When mif was added in addition to MDV3100 treatment, there was a synergistic impairment of cell survival. For LAPC4 cells, compared to R1881+Dex control, there was no change in survival with the addition of Mif alone, but a significant 26% and 52% reduction in cell death with MDV3100 and MDV3100+Mif respectively.

To test if SGK1 was required for GR-mediated protection from cell death following AR inhibition, the cell lines were grown with or without GSK650394. Cell survival with both cell lines was impaired following treatment with the SGK1 inhibitor. For LAPC4, relative to R1881+Dex control, % survival was 58% with MDV3100+Dex and only 19% with the addition of GSK650394 (p<0.05). Results with the 22RV1 cells were similar. SGK1-Flag over-expressing LAPC4 cells were protected from MDV3100 treatment compared to vector controls—61% vs. 24% survival (p<0.05). These data suggest that increased GR expression and activity antagonizes AR inhibition and sustains tumor cell survival. Furthermore, SGK1 appears to be a downstream mediator of this effect.

In conclusion, the inventors have shown that in the context of first line ADT, the expression of glucocorticoid receptor (GR) within human prostate cancer specimen increases compared to those who have not been treated with ADT. With the understanding that CRPC is driven by AR signaling, and that second generation AR inhibitors such as MDV3100 potently inhibit the AR in this setting, the inventors set out to test if GR activation could potentially compensate for reduced AR function in the setting of CRPC treated with MDV3100 thereby leading to resistance to the anti-AR therapy. The preclinical data to date support the notion that increased GR activity in CRPC treated with AR inhibitors such as MDV3100 can compensate for diminished AR activity and can protect CRPC cells from MDV3100 (and other AR inhibitor)-associated cell death. In the inventors' preclinical models with CRPC cell lines, the addition of MDV3100 significantly increases GR expression level within 3-7 days. Furthermore, with the addition of a GR inhibitor, such as mifepristone, the GR activity can be overcome, restoring the decrease in proliferation seen with MDV3100 in the absence of GR activation. Clinically, this has high-level potential implications. CRPC patients have endogenous circulating and local hormones (glucocorticoids) that can activate the GR at baseline. Furthermore, CRPC patients are often treated with higher doses of synthetic glucocorticoids used for their anti-inflammatory properties. Thus, CRPC patients who are treated with MDV3100 may have activated GR within their prostate cancers that could drive resistance to AR inhibition based on the data described above. Thus, the inventors believe that a GR inhibitor will synergize with second generation AR-inhibitors, such as MDV3100, and delay the onset of CRPC progression in patients treated with the combination compared to patients treated with MDV3100 alone.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

Belova et al., *Breast Cancer Res. Treat.,* 116(3):441-447, 2009.
Bolton et al., *Genes Dev.,* 21(16):2005-2017, 2007.
Chan et al., *Urology,* 56(5):823-827, 2000.
Chen et al., *J. Biol. Chem.,* 272(22):14087-14092, 1997.
Cleutjens et al., *Endocrinology,* 138(12):5293-5300, 1997.
De Bono et al., *N Engl. J. Med.,* 364(21):1995-2005, 2011.
Donovan et al., *BJU Int.,* 105(4):462-467, 2010.
Fakih et al., *Urology,* 60(4):553-561, 2002.
Fiorentino et al., *Urol. Clin. North. Am.,* 37(1):131-141, 2010.
Fradet, *Curr. Opin. Urol.,* 19(3):243-246, 2009.
Guo et al., *Cancer Res.,* 69(6):2305-2313, 2009.
Han et al., *J Urol.,* 169(2):517-523, 2003.
Harrison's Principles of Internal Medicine, Kasper et al. (Eds.), 16th Ed., Chapter 70, 2005.
Ho et al., *J. Biol. Chem.,* 268(36):27226-27235, 1993.
Jemal et al., *CA Cancer J Clin.,* 60(5):277-300, 2010.
Klein et al., *Stat. Med.,* 26(24): 4505-4519, 2007.
Koochekpour, *Asian J Androl.,* 12(5):639-657, 2010.
Li et al., *Am. J Surg. Pathol.,* 28(7):928-934, 2004.
Lotan et al., *J. Pathol.,* 212(4):386-394, 2007.
Makarov et al., *Urology,* 69(6):1095-1101, 2007.
Mikosz et al., *J. Biol. Chem.,* 276(20):16649-16654, 2001.
Mohler et al., *Clin. Cancer Res.,* 2(5):889-895, 1996.
Niemeier et al., *Mod. Pathol.,* 23(2): 205-212, 2010.
Petrylak et al., *J. Natl. Cancer Inst.,* 98(8):516-521, 2006.
Pound et al., *JAMA,* 281(17): 1591-1597, 1999.
Rauhala et al., *Int. J Cancer,* 117(5):738-745, 2005.
Remington's Pharmaceutical Sciences, 15th Ed., 1035-1038 and 1570-1580, 1990.
Rosner et al., *Urology,* 70(6):1225-1229, 2007.
Sahoo et al., *Eur. J Cancer,* 41(17):2754-2759, 2005.
Scher and Sawyers, *J. Clin. Oncol.,* 23(32): 8253-8261, 2005.
Szmulewitz et al., *Prostate,* 72(2): 157-64, 2012.
Shanmugam et al., *Cell Death Differ.,* 14(12):2085-2094, 2007.
Sherk et al., *Cancer Res.,* 68(18):7475-7483, 2008.
Stephenson et al., *J. Natl. Cancer Inst.,* 98(10):715-717, 2006.
Sterbis et al., *Clin. Cancer Res.,* 14(3):758-763, 2008.
Sun et al., *J. Clin. Invest.,* 120(8):2715-2730, 2010.
Tannock et al. *N. Engl. J. Med.,* 351(15):1502-1512, 2004.
Tessier add Woodgett Jr., *J. Cell Biochem.,* 98(6):1391-1407, 2006.
Ward and Moul, *Nat. Clin. Pract. Urol.,* 2(4):174-182, 2005.
Wright et al., *J. Urol.,* 182(6):2702-2707, 2009.
Wu et al., *Cancer Res.,* 64(5):1757-1764, 2004.
Yemelyanov et al., *Oncogene,* 26(13):1885-1896, 2007.
Zegarra-Moro et al., *Cancer Res.,* 62(4):1008-1013, 2002.
Zou et al., *Cancer Res.,* 69(8):3339-3346, 2009.

What is claimed is:

1. A method of treating prostate cancer in a subject comprising co-administering to said subject a glucocorticoid receptor (GR) antagonist and a drug or treatment that decreases circulating levels of testosterone (androgen deprivation therapy), wherein said subject exhibits androgen-deprived prostate cancer, and wherein said subject has previously been or is being treated with androgen deprivation therapy, wherein said androgen deprivation therapy comprises treatment with leuprolide, goserelin, triptorelin, histrelin degerelix or surgical castration, and wherein said subject has been or is being treated with an androgen receptor (AR) antagonist.

2. The method of claim 1, wherein the AR antagonist is MDV3100, ARN-509, flutamide, bicalutamide, nilutamide, or cyproterone acetate.

3. The method of claim 1, wherein said subject exhibits prostate cancer with elevated GR expression.

4. The method of claim 1, wherein said GR antagonist is beclometasone, betamethasone, budesonide, ciclesonide, flunisolide, fluticasone, GSK650394, mifepristone, mometasone, or triamcinoclone.

5. The method of claim 1, wherein said subject is treated with a second prostate cancer therapy.

6. The method of claim 1, wherein said subject is treated with surgical castration.

7. The method of claim 5, wherein said second prostate cancer therapy comprises administration of an androgen receptor (AR) antagonist.

8. The method of claim 7, wherein the AR antagonist is MDV3100, ARN-509, flutamide, bicalutamide, nilutamide, or cyproterone acetate.

9. The method of claim 5, wherein said second prostate cancer therapy is conventional chemotherapy, radiotherapy, cryotherapy, immunotherapy or surgery.

10. The method of claim 1, wherein said drug or treatment that decreases circulating levels of testosterone is given prior to said GR antagonist.

11. The method of claim 1, wherein said drug or treatment that decreases circulating levels of testosterone is given after said GR antagonist.

12. The method of claim 1, wherein said drug or treatment that decreases circulating levels of testosterone is given at the same time as said GR antagonist.

13. The method of claim 1, wherein said prostate cancer is metastatic or recurrent prostate cancer.

\* \* \* \* \*